United States Patent
Löwen et al.

(10) Patent No.: US 11,992,400 B2
(45) Date of Patent: May 28, 2024

(54) STENT GRAFT AND METHOD FOR PRODUCING SAME

(71) Applicant: RHEINISCH-WESTFÄLISCHE TECHNISCHE HOCHSCHULE (RWTH) AACHEN, Aachen (DE)

(72) Inventors: Alexander Löwen, Aachen (DE); Valentine Gesché, Aachen (DE); Stefan Jockenhövel, Aachen (DE); Thomas Gries, Aachen (DE)

(73) Assignee: Rheinisch-Westfalische Technische Hochschule Aachen, Aachen (DE)

( * ) Notice: Subject to any disclaimer, the term of this patent is extended or adjusted under 35 U.S.C. 154(b) by 582 days.

(21) Appl. No.: 17/255,844

(22) PCT Filed: Jun. 25, 2019

(86) PCT No.: PCT/EP2019/066906
§ 371 (c)(1),
(2) Date: Dec. 23, 2020

(87) PCT Pub. No.: WO2020/002371
PCT Pub. Date: Jan. 2, 2020

(65) Prior Publication Data
US 2021/0251740 A1    Aug. 19, 2021

(30) Foreign Application Priority Data
Jun. 26, 2018 (DE) .................... 10 2018 005 070.0

(51) Int. Cl.
*A61F 2/07* (2013.01)
*B33Y 10/00* (2015.01)
(Continued)

(52) U.S. Cl.
CPC ............... *A61F 2/07* (2013.01); *B33Y 10/00* (2014.12); *B33Y 50/00* (2014.12); *B33Y 80/00* (2014.12);
(Continued)

(58) Field of Classification Search
CPC ............... A61F 2/07; A61F 2210/0014; A61F 2210/0071; A61F 2240/001;
(Continued)

(56) References Cited

U.S. PATENT DOCUMENTS 5,800,514 A * 9/1998 Nunez .................... D03D 3/02
139/389
5,911,753 A    6/1999 Schmitt
(Continued)

FOREIGN PATENT DOCUMENTS

DE    10 2015 207 596 A1    10/2016
GB    2 347 861 A    9/2000
WO    WO-2016/116748 A1    7/2016

OTHER PUBLICATIONS

International Search Report and Written Opinion of the International Searching Authority issued in International Application No. PCT/EP2019/066906, dated Oct. 9, 2019.
(Continued)

*Primary Examiner* — Mohamed G Gabr
(74) *Attorney, Agent, or Firm* — Foley & Lardner LLP

(57) ABSTRACT

The invention relates to a method for producing a stent graft. The method comprises providing a graft made of a first polymer-based material and applying a stent structure comprising a plurality of struts made of a second polymer-based material onto the graft by means of an additive manufacturing method. The invention further relates to a stent graft produced by means of the method.

29 Claims, 2 Drawing Sheets

(51) Int. Cl.
*B33Y 50/00* (2015.01)
*B33Y 80/00* (2015.01)

(52) U.S. Cl.
CPC . *A61F 2210/0014* (2013.01); *A61F 2240/001* (2013.01)

(58) Field of Classification Search
CPC ... A61F 2240/002; B33Y 10/00; B33Y 50/00; B33Y 80/00
See application file for complete search history.

(56) References Cited

U.S. PATENT DOCUMENTS

| | | |
|---|---|---|
| 2001/0056299 A1 | 12/2001 | Thompson |
| 2004/0193258 A1 | 9/2004 | Ellis et al. |
| 2007/0061004 A1 | 3/2007 | Steinke et al. |
| 2007/0293936 A1 | 12/2007 | Dobak, III |
| 2008/0082160 A1 | 4/2008 | Boyden et al. |
| 2009/0043330 A1 | 2/2009 | To |
| 2009/0125100 A1* | 5/2009 | Mead ............... A61F 2/954 623/1.13 |
| 2011/0009948 A1 | 1/2011 | Huang et al. |
| 2012/0197382 A1 | 8/2012 | Roeder |
| 2013/0296998 A1 | 11/2013 | Leotta et al. |
| 2013/0331927 A1 | 12/2013 | Zheng et al. |
| 2015/0265438 A1* | 9/2015 | Hossainy ........... A61L 31/041 623/1.11 |
| 2015/0306282 A1* | 10/2015 | Scanlon ............. A61L 31/18 623/1.34 |
| 2015/0320956 A1 | 11/2015 | Dunne |
| 2015/0335451 A1 | 11/2015 | Liu et al. |
| 2017/0333133 A1 | 11/2017 | Van Bibber et al. |

OTHER PUBLICATIONS

Yakacki et al., "Unconstrained recovery characterization of shape-memory polymer networks for cardiovascular applications", Biomaterials, 2007, pp. 2255-2263, vol. 28, Elsevier Ltd.

* cited by examiner

STENT GRAFT AND METHOD FOR PRODUCING SAME

RELATED APPLICATIONS

The present application claims priority under 37 U.S.C. § 371 to International Patent Application No. PCT/EP2019/066906, filed Jun. 25, 2019, which claims priority to and the benefit of German Patent Application No. 10 2018 005 070.0, filed on Jun. 26, 2018. The contents of these applications are hereby incorporated by reference in their entireties.

The present invention relates to a stent graft and a method for producing it, wherein in particular a stent structure is applied onto a graft by means of an additive method.

Vessels, in particular blood vessels, may change over time due to numerous factors, including aging, nutrition, stress or disease. Changes in respect of the elasticity and stability of the vessel walls, which often affect the diameter of the vessels, and changes in respect of the function of valves are particularly risky.

There are various known ways to reduce the threat posed by vascular changes. Vascular implants, which bridge or even replace the corresponding vessel section, are often used. For example, a locally constricted vessel may be replaced by a bypass or a pathologically dilated vessel may be bridged or replaced by a stent graft.

Stent grafts are hollow cylinders having a longitudinal extension and comprising a tubular graft and a usually metal stent structure for stabilizing the graft. The stent structure and the graft are usually produced in separate manufacturing processes and subsequently assembled in a relatively time-consuming and cost-intensive way by means of partly still manual steps, for example, by suturing. Examples of such vascular implants are known, for example, from GB 2 347 861 A, US 2004/193258 A1 or U.S. Pat. No. 5,911,753 A, and available products are already being used routinely.

However, as regards the individual vessel geometry, patient-specific solutions are desirable in addition to clinically established standard products. However, these patient-specific solutions are still associated with comparatively high manufacturing costs and time-consuming production steps.

A method for the generation of a vascular support based on a digital 3D model is known from DE 10 2015 207 596 A1. A plurality of layers are applied on top of each other, in particular by means of a (PolyJet) process. However, it seems doubtful that the manifold clinical requirements placed on such a vascular support can be met in this way.

Moreover, the production of a hybrid polymer stent is known from US 2015/0335451 A1. However, these stents have apparently not become established in practice either.

Further examples of stent grafts and the production thereof are set forth below, wherein according to the state of the art, for example, the stent structure may be produced by an additive method.

For example, US 2007/061004 A1 provides a lumen support stent with a clear through-lumen for use in a body lumen. Said stent is formed from at least one series of sliding and locking radial elements and at least one ratcheting mechanism comprising an articulating element and a plurality of stops. The ratcheting mechanism permits one-way sliding of the radial elements from a collapsed diameter to an expanded diameter, but inhibits radial recoil from the expanded diameter.

US 2009/043330 A1 provides a PreStent comprising a sheath and frame designed for preparing a vessel passageway for the subsequent delivery of a stent, wherein the PreStent may be self-expanding or balloon-expandable. Also provided is a supporting system for delivering the PreStent safely, wherein the supporting system includes a delivery catheter, one or more occlusion balloons, optionally one or more dilation balloons and a retention sheath for the self-expanding type of PreStent.

US 2017/333133 A1 provides a method of generating a patient-specific prosthesis, which includes receiving anatomic imaging data representative of a portion of a patient's anatomy. Furthermore, a first digital representation of the anatomic imaging data is defined, modified, and based thereon a second digital representation of the portion of the patient's anatomy is defined. A patient-specific prosthetic template of the portion of the patient's anatomy is generated based at least in part on the second digital representation of the anatomic imaging data.

US 2012/197382 A1 provides an endoluminal prosthesis, which comprises a graft having a tubular body comprising proximal and distal ends, and a valve replacement disposed between the proximal and distal ends of the graft. At least one stent is coupled to the graft and has a contracted delivery state and an expanded state for maintaining patency within a portion of the graft.

Against this background, the present invention aims at providing an automatable, time- and cost-efficient method that simplifies the production of stent grafts and in particular customized stent grafts. The invention also aims at ensuring that the manufactured stent grafts have a high biocompatibility and meet the requirements in the clinical practice. These include, inter alia, sufficient crimpability and/or foldability for endovascular insertion and/or sufficient radial stiffness in an expanded state.

According to the invention, this is achieved by a method and a stent graft according to the attached claims, wherein preferred embodiments are mentioned in the dependent claims.

The stent graft according to the invention comprises a graft and a stent structure that is preferably applied directly onto the graft by means of an additive method. The stent structure is preferably polymer-based and/or made of a polymeric material.

The method for producing the stent graft according to the invention comprises providing a graft preferably made of a first polymer-based material, and applying a stent structure comprising a plurality of struts made of a second polymer-based material onto the graft by means of an additive method, preferably by means of fused deposition modeling. The graft and the applied stent structure are preferably configured such that the stent graft can be arranged in at least one compressed state and in at least one expanded state, wherein the stent graft has a smaller cross-section in the at least one compressed state than in the at least one expanded state.

Thus, according to the method according to the invention, not only is the stent structure produced by means of an additive method, as already known from the state of the art, but rather the stent structure is applied directly onto the graft by means of an additive method, preferably by means of fused deposition modeling. In this way, the production of stent grafts, in particular also of customized stent grafts, can be automatedly, time- and cost-efficiently performed and it can be ensured that the preferably metal-free stent graft respectively produced meets the requirements in the clinical practice particularly well. Thus, it is possible to avoid in particular prior art methods of applying a stent structure onto a graft, such as suturing, bonding or welding.

In the context of the present invention, the term "stent graft" refers to an endovascular vascular implant or an endovascular vascular prosthesis comprising at least one stent structure and at least one graft attached thereto. Here, the term "stent structure" means a structure which preferably comprises a plurality of struts. The stent structure is preferably tubular and/or tube-shaped. The term "graft" denotes a structure that channels a medium within a vessel lumen. The graft is preferably connected to a stent structure, for example, in the form of a lining and/or sheath of the stent structure. Such a sheath is preferably tubular and/or tube-shaped. The sheath is preferably made of a polymer-based and/or polymeric material.

The term "stent graft" used here preferably denotes a stent structure with a graft attached thereto and thus comprises any type of endovascular vascular implant that at least temporarily comprises at least one preferably tubular structure comprising a plurality of struts and at least one preferably polymer-based material layer as a sheathing component.

In the context of the present invention, the term "vessel" denotes any type of tubular body structure, in particular of the human body, which transports at least one fluid such as a gas and/or a liquid, not exclusively but in particular hollow vessels such as, for example, blood vessels. The vessel may be located in different regions of the body, for example, in the extremities or in the brain, but in particular in the abdomen and/or thorax. In the following, a vessel exhibiting a genetically determined and/or acquired vessel wall alteration is referred to as an affected vessel. The term affected area relates to the locally restricted area of the vessel wall alteration in the affected vessel as well as to directly adjacent areas. In the following, the term "intact" denotes conditions, geometry and/or properties that the vessel would have and/or has had in the affected area without a vessel wall alteration, taking into account various factors such as, for example, age, sex and/or body weight. For example, conditions, geometry and/or properties of the vessel areas directly adjacent to the area of the vessel wall alteration may also be taken into account. Furthermore, changes in a vessel wall are referred to as aneurysms, wherein various definitions of the term "aneurysm" are known to the person skilled in the art. For example, changes in a vessel wall which lead to an increase in the diameter of the affected vessel, generally to an increase of at least 50% compared to the diameter of an intact vessel in the respective area, may be referred to as an aneurysm. The absolute diameter of a vessel in the area of the vessel wall alteration may also be used as an indication of an aneurysm, for example, in the case of an abdominal aorta of 5 cm to 5.5 cm in men and 4.5 cm to 5 cm in women. In the case of other vessels, such as thoracic or thoraco-abdominal aortas, corresponding values, possibly with a slight deviation, may also be used as an indication of an aneurysm. As the case may be, the increase in vessel diameter may also be smaller, in particular if the alteration is progressing comparatively fast. For example, the increase in vessel diameter of at least 5 mm within 6 months may indicate an increased risk of rupture and/or an aneurysm of the affected vessel.

The stent graft may be configured to treat aneurysms. In particular, the stent grafts according to the invention may be stent grafts for the treatment of aortic aneurysms, such as, for example, for the treatment of aneurysms of the thoracic, thoraco-abdominal or abdominal aorta.

According to the invention, the at least one stent structure is applied onto the at least one material layer of the graft by means of an additive method. In the context of the present invention, the term "additive method" includes additive manufacturing methods or methods for additive or generative manufacturing which are known to the person skilled in the art and in which elements are automatedly manufactured by joining materials on top of each other or to each other. Additive methods include, for example, 3D printing methods as well as methods depositing fused material layer by layer (e.g., fused deposition modeling). In fused deposition modeling, the preferably polymer-based material of the stent structure is liquefied, for example, by means of a heated nozzle and applied onto the graft in the form of filaments in one or more layers, preferably immediately and/or directly onto the graft. The material may be fed to the nozzle as a filament. Alternatively, the material may be provided as granules, which are melted by an extruder and fed to the nozzle.

The provided graft is preferably tubular and/or tube-shaped, wherein the graft may be funnel-shaped and/or may comprise diameter jumps and/or may comprise bifurcations/branches. Preferably the graft is cylindrical. Thus, the stent structure is preferably applied onto a cylindrical graft. However, the graft could also be provided as a layer of material, e.g., as a flat layer of material. In this case, after applying the stent structure, the graft comprising the stent structure applied onto it could be formed into a tubular shape, for example, by sewing, bonding, welding, or fusing.

The stent structure is preferably applied onto the graft by using a rotatable holder by means of which the graft can be held and rotated, preferably about its longitudinal axis. Such a holder may be, for example, a rotating tubular core and/or a rotating tubular framework on the outer surface of which the provided graft rests. In this case, the at least one stent structure is preferably applied onto the outside of the graft. If the applied stent structure is to be arranged inside the graft, the method according to the invention may comprise a further, optional step of inverting the stent graft. The graft of the stent graft according to the invention may therefore be provided such that it encases the stent structure from inside or outside.

Furthermore, the stent graft according to the invention may comprise at least one stent structure that is arranged on the graft at least partially inside and outside. Optionally or alternatively, the stent graft according to the invention may comprise at least one stent structure that is arranged on an inner side of the graft and at least one stent structure that is arranged on an outer side of the graft. Respective stent structures may be arranged on a graft such that a respective area of the stent graft according to the invention that comprises at least one stent structure on the inside of the graft simultaneously comprises at least one stent structure on the outside of the graft. Alternatively, respective stent structures may be arranged on the graft such that at least one area of the stent graft according to the invention that comprises at least one stent structure on an inner side of the graft, simultaneously comprises at least one stent structure on an outer side of the graft. Furthermore, alternatively, respective stent structures may be arranged on the graft such that a respective area of the stent graft according to the invention that comprises a stent structure on an inner side of the graft does not comprise a stent structure on an outer side of the graft. The respective stent structures that are arranged on an inner side and/or on an outer side of the stent graft thus preferably do not overlap or only partially overlap in the longitudinal direction of the stent graft. Preferably, the stent graft according to the invention comprises at least one stent structure that is arranged in at least one area of a tubular end of the stent graft on its inside and at least one stent structure that is arranged in at least one central area of the tubular stent graft on its outside.

According to the invention, such stent grafts can be produced, for example, by applying at least one first stent structure onto a graft, preferably by using a rotatable holder as also described above. The method according to the invention preferably further comprises a step of inverting the graft comprising the at least first applied stent structure, followed by at least one further step of applying at least one further stent structure as described above, wherein the respective at least one stent structure may be arranged in one or more areas of the graft or may surround it over the entire length and/or the entire circumference.

The graft is preferably polymer-based. In the context of the present invention, the term "polymer-based" comprises the expressions "comprising at least one polymer", "consisting of a proportion of at least one polymer", wherein the proportion accounts for up to 50% or up to 70%, preferably up to 75% or up to 80% and particularly preferably up to 90% or up to 95%, as well as "made of at least one polymer" or "consisting of 100% of at least one polymer".

Alternatively or additionally, the graft is preferably a textile and/or textile-based. To generate such a textile, techniques and materials known to the person skilled in the art may be used, wherein the provided graft is preferably made of biocompatible and/or hemocompatible materials, such as polytetrafluoroethylene (PTFE), polyethylene terephthalate (PET), polyvinylidene fluoride (PVDF), polyurethane (PU), polylactide (PLA) and/or polycaprolactone (PCL). Alternatively or additionally, the provided graft is preferably configured as a weave and/or knitwear. In this context, a weave is preferably understood to be a woven fabric that is produced by crossing at right angles at least two thread systems, whereas knitwear is understood to be a weft- and warp-knitted fabric that comprises one or more intertwined threads. For the production of the graft, for example, monofilament and/or multifilament yarns may be used as threads. In terms of the total yarn count of the thread, the threads may have a fineness of 1 dtex to 200 dtex, preferably of 10 dtex to 60 dtex, for example, according to EN ISO 2060:1995, preferably according to Variant 1 referred to as Principle under point 4, or for monofilaments, for example, according to EN 13392:2001. After its production, for example, the graft may have a material layer thickness of 0.01 mm to 2 mm, preferably of 0.1 mm to 0.5 mm, preferably optically measured on the stent graft.

The provided graft preferably comprises knitwear and/or is formed of such a knitwear.

This knitwear may be produced in particular by means of the double raschel technique, wherein said technique is preferably a jacquard technique. This technique allows a particularly flexible adaptation of the graft to the anatomy of the respective patient.

The provided graft preferably comprises a plurality of pores, for example, more than 100 or more than 1,000 pores, which are formed by thread interstices of the textile, in particular by the meshes between the thread/threads, wherein the respective thread/threads may be formed by several filaments. The size and the opening area of the pores are therefore easily adjustable. Preferably, the graft has a mesh or pore size of 1 μm to 1,000 μm, more preferably of 10 μm to 300 μm. Therefore, the individual pores may comprise an opening area of 1 to 1,000,000 μm$^2$, preferably of 100 to 90,000 μm$^2$.

The pores of the graft may be equal and/or different in size and, for example, may also vary in size in the direction of flow along the stent graft. This can support, for example, a stable positioning of the graft in the vessel by ingrowth of tissue into the pores.

The provided graft may be configured to be permeable to liquid. In this case, the graft preferably forms a self-sealing system, wherein the liquid transported in the vessel seals the graft after implantation of the stent graft, for example, by coagulation of components contained in the liquid in and/or on the graft. To this end, the pore sizes may be selected such that, when the stent graft is implanted in a blood vessel, they can be sealed, for example, by a deposition of fibrin on the graft during blood coagulation. However, the provided graft may also be impermeable to liquid, for example in that the graft is coated with collagen and/or gelatin. A respective coating may be applied onto a graft before the application of a stent structure onto the graft. In this case, the method according to the invention comprises a step of coating the graft before the application of a stent structure onto the graft. Alternatively, a respective coating may be applied onto a graft after the application of a stent structure onto the graft. In this case, after the application of a stent structure onto the graft, the method according to the invention comprises a step of coating the produced stent graft.

The stent structure can support the graft and is preferably compressible to place the stent graft in the at least one compressed state and/or expandable to place the stent graft in the at least one expanded state. To this end, the stent structure may be elastically deformable and/or comprise at least one smart polymer. Alternatively or additionally, the stent structure may be mechanically expandable, for example, via a balloon catheter.

The struts of the stent structure may be arranged in different configurations, wherein they preferably form a compressible helical, zigzag or mesh structure, optionally and/or alternatively also meander-shaped rings (crowns). In order to compress the stent structure, the opening angle between two struts connected to each other at a junction and/or intersection point may preferably be reduced. A corresponding compression of the stent structure may also be referred to as "crimping".

In the context of the present invention, smart polymers denote polymers which are characterized by their sensitivity to at least one external factor, such as temperature, humidity, pH value, light intensity, electric fields and/or magnetic fields, and which change at least one physical property, preferably reversibly and preferably rapidly, in response to at least one of these external factors. Preferred smart polymers are, for example, co-block polymers, which, if need be, may also be used to release active ingredients.

Preferably, the stent structure comprises at least one shape memory polymer. Shape memory polymers, as smart polymers, in particular have the property of changing their shape in a predefined way in response to at least one of the mentioned external factors. Examples of preferred shape memory polymers are polyurethane (PU)-based polymers. Preferably, a shape memory polymer is used that returns to a previously trained shape when a certain temperature is reached, for example, at a temperature above 30° C., above 35° C., above 37° C., above 40° C. or above 45° C. (for example, Yakacki et al., Biomaterials, 2007, 28:2255-63). The recovery into the trained form is preferably achieved at a temperature of below 55° C., below 50° C., below 45° C. or below 40° C.

The stent structure may comprise at least one non-smart, biocompatible polymer and/or at least one additive in addition to or as an alternative to the at least one smart polymer. In the context of the present invention, additives denote admixtures known to the person skilled in the art which modify the properties of the used polymer, for example, organic fillers, e.g., carbon fibers, or inorganic fillers, e.g., silicates. In the context of the present invention, non-smart, biocompatible polymers denote polymers known to the person skilled in the art which are suitable for use as implants, in particular polyethylene terephthalate (PET), polytetrafluoroethylene (PTFE), polyvinylidene fluoride (PVDF) and polyetheretherketone (PEEK) and thermoplastic polyurethane (TPU). By the selection of the at least one polymer-based material used for the stent structure, the compressibility and the radial stiffness in the expanded state of the produced stent graft can be adjusted. Moreover, the polymer may be selected such that sufficient adhesion between the stent structure and the graft is achieved, depending on the additive manufacturing method and the material of the graft. Alternatively or additionally, the graft may be temperature-controlled and/or the build envelope of the 3D printer may be temperature-controlled to achieve an improved adhesion between the stent structure and the graft. The set temperature may be, for example, in the range of the glass transition temperature of the printed polymer. A combination of polymers having different material properties is also possible. Such a combination may be provided, for example, by compounding. Alternatively and/or additionally, polymers having different material properties may be combined during additive manufacturing, for example, by printing different layers, using several nozzles and/or using bicomponent nozzles. The material and/or the processing conditions (such as the temperature) may be selected such that the material of the stent structure at least partially flows into the pores of the graft and/or flows through from one side of the graft to the other. Alternatively or additionally, the material and/or its processing conditions (such as the temperature) may be selected such that at least some threads of the graft are embedded in the material of the stent structure and/or are completely surrounded by the material of the stent structure along sections of the thread length.

The configuration of the stent structure is freely selectable and customizable by means of additive manufacturing, in particular in the case of fused deposition modeling. For example, the filaments to be fused may have a diameter of 0.5 mm to 3.5 mm, preferably 1 mm to 3 mm and particularly preferably 1.75 mm to 2.85 mm.

The stent structure preferably comprises a plurality of struts connected to each other, wherein, as seen in a cross-section perpendicular to the direction in which the respective strut extends, the struts have a height of at least 0.01 mm, preferably at least 0.05 mm or at least 0.1 mm in the radial direction of the stent graft. For example, the struts may have a height of 0.01 mm to 3 mm, preferably 0.05 mm to 1 mm. Alternatively or additionally, the struts may have a width perpendicular to the height of at least 0.01 mm, preferably at least 0.05 mm or 0.1 mm in this cross-section. For example, the struts may have a width of 0.01 mm to 5 mm, preferably of 0.01 mm to 3 mm, particularly preferably of 0.05 mm to 1 mm.

The struts, as seen in a cross-section perpendicular to the direction in which the respective strut extends, may be built from a plurality of layers in the radial direction of the stent graft (height direction of the respective strut). The thickness of an individual layer may be 0.005 mm to 1 mm, preferably 0.01 mm to 0.7 mm and particularly preferably 0.02 mm to 0.4 mm. Alternatively or additionally, the struts, as seen in a cross-section perpendicular to the direction in which the respective strut extends, may be built from a plurality of layers perpendicular to the radial direction of the stent graft (width direction of the respective strut), e.g., of a plurality of lines extruded side by side. The extrusion width of a single line may be 0.01 mm to 5 mm, preferably 0.05 mm to 2 mm and particularly preferably 0.1 mm to 1 mm or 0.1 mm to 0.5 mm. Alternatively or additionally, the individual extruded lines may overlap in the width direction, for example, by at most 70%, preferably by at most of 50% and particularly preferably by at most of 30%.

The struts may be arranged in configurations known to the person skilled in the art, for example, in zigzag- and/or meander-shaped rings (crowns), spirally and/or in zigzag-shaped spirals. The spirals and/or rings may in turn be connected to each other via connectors. The struts may be provided such that they cover in the expanded state at most 50%, at most 40%, at most 30%, at most 20%, at most 12%, at most 10%, at most 8%, at most 6%, at most 5% or at most 3% of the inner lateral surface area of the graft and/or at most 50%, at most 40%, at most 30%, at most 20%, at most 12%, at most 10%, at most 8%, at most 6%, at most 5% or at most 3% of the outer lateral surface area of the graft. Furthermore, the struts may be provided such that they cover in the expanded state at least 12%, at least 10%, at least 8%, at least 5%, at least 3% or at least 1% of the inner lateral surface area of the graft and/or at least 12%, at least 10%, at least 8%, at least 5%, at least 3% or at least 1% of the outer lateral surface area of the graft.

In the preferred use of the fused deposition modeling, the stent structure may further have a structure in which structural elements such as coils are formed without intersections of the filaments. Furthermore, the stent structure preferably does not exhibit any subsequently induced local changes in the material properties such as seams, weld zones and/or adhesive residues.

The stent graft according to the invention is preferably configured such that it supports, bridges and/or replaces the area affected by a change. For example, the stent graft preferably exhibits sufficient structural stability and elasticity to ensure the functionality of the vascular implant over a long period of time, for example, at least 1 year, at least 5 years, at least 10 years or at least 15 years. The stent graft may be configured such that its diameter may vary along with the intact vascular areas throughout the heart rhythm. However, according to a preferred embodiment, the stent graft is configured such that its diameter does not vary significantly throughout the heart rhythm. The stent graft is preferably metal-free. Both the graft and the stent structure may be biodegradable, wherein the graft and the stent structure may be biodegradable at the same or different rates. However, in a preferred embodiment of the stent graft according to the invention, the graft and the stent structure are not biodegradable. Furthermore, the stent graft may also comprise a plurality of identical or different stent structures and/or grafts and/or include further components applied onto the at least one stent structure and/or the at least one graft, such as, for example, one or more coatings. Such components may be biodegradable and/or comprise biocompatible materials and/or be coated therewith. The stent graft may comprise one or more coatings, such as silicone, collagen and/or gelatin.

The stent graft according to the invention may be inserted into the respective vessel in various ways, in particular endovascularly and/or minimally invasively. For example, the stent graft may be in the compressed state when it is inserted into the affected vessel, said compressed state preferably having a smaller cross-section than the affected vessel and, should the situation arise, other vessels to be passed during the insertion of the stent graft. The at least one compressed state has a diameter of 1 to 20 mm, preferably of 2 to 15 mm and particularly preferably of 4 to 10 mm. A smaller cross-section may be achieved in particular by reducing the cross-sectional area by more than 30%, preferably by more than 50% and particularly preferably by more than 80% compared to the at least one expanded state. At the target site, the stent graft may be released and/or deployed, followed by a preferably reversible state to the expanded state, wherein the expanded state has a diameter that approximately corresponds to the diameter of the intact vessel in the affected area. The at least one expanded state thus has a diameter of 0.5 cm to 6 cm, preferably of 0.7 cm to 5 cm and particularly preferably of 1 cm to 4 cm. The at least one expanded state may have a diameter of at least 0.5 cm, at least 1 cm, at least 2 cm or at least 3 cm.

The stent graft may have a constant diameter along its length or a diameter that tapers in the direction of flow, depending, for example, on the individual vessel geometry.

The transition of the stent graft from the compressed to the expanded state may be achieved by release from a catheter system limiting the diameter and/or by balloon dilatation. Alternatively or additionally, it may be prompted by an external factor such as, for example, humidity, pH value, light intensity, electric fields, magnetic fields and/or in particular by a permanent and/or at least short-term change in temperature. Such a permanent and/or at least short-term change in temperature may be passively achieved by the difference between the room temperature and the temperature prevailing in the vessel. The change from the at least one compressed state to the at least one expanded state is preferably prompted by a short-term temperature increase to values between 30° C. and 60° C., preferably between 33° C. and 50° C. and particularly preferably between 35° C. and 40° C. This temperature increase may be an increase in the ambient temperature due to the body temperature itself. A change in temperature may be additionally and/or alternatively also actively prompted, for example, by flushing a catheter system and/or the vessel with temperature-controlled saline solution, e.g., to prevent a premature change in state during the insertion and positioning of the stent graft.

The stent graft is preferably configured such that it rests against the vessel wall, in particular an intact portion of the vessel wall, along a sufficient length and thus is stably positioned at the desired position. To this end, the stent graft may have, for example, a length of 1 cm to 35 cm, but preferably between 1 cm and 30 cm, particularly preferably between 5 cm and 25 cm. The length of the stent graft may be at least 3 cm, at least 4 cm or at least 5 cm. The length of the stent graft may be less than 30 cm, less than 20 cm or less than 15 cm.

For the purpose of a stable positioning, contact surfaces for resting against the intact vessel wall, the so-called landing zone, may be formed in end regions at the at least two open ends of the hollow-cylindrical shape of the stent graft, but at least in the end region of the end that is located upstream in the direction of flow. The respective contact surface preferably has a length between 0.1 cm to 5 cm, preferably between 0.5 cm to 2 cm. Optionally, the stent graft may also comprise hooks or other elements for anchoring and/or positioning the stent graft in the affected area, for example, at the end that is located upstream in the direction of flow. Thereby, a particularly strong anchoring can be achieved.

Routinely used stent grafts are usually generalized standard products. For the purpose of a stable positioning in close proximity to the area of the altered vessel wall, these generalized standard products usually require an intact and continuous vessel wall having a length of at least 10 to 15 mm. However, if the vessel wall alteration is at or near a bifurcation, the use of such standard products may be excluded, as they would interrupt the blood supply to the branching vessel. Abdominal aortic aneurysms (AAA) or aneurysms of the thoracic aorta (TAA) as well as aneurysms that extend across both of the above-mentioned areas (thoraco-abdominal aortic aneurysms (TAAA)) often occur in the vicinity of such vessel bifurcations, such as, for example, the renal arteries. Therefore, the stent graft may comprise further openings in addition to the open ends of its tubular structure, wherein, if necessary, said further openings may also be configured to be expandable.

The provided graft may comprise one or more scallops and/or fenestrations to form these openings. The term scallop denotes a clearance at one end of the preferably tubular and/or tube-shaped graft. Preferably, the term scallop denotes a triangular, preferably quadrangular or U-shaped clearance at the end located upstream in the direction of flow of the graft. In this context, a scallop has a clearance height of 3 mm to 20 mm, preferably 5 mm to 15 mm, measured in the direction of flow, and a width (preferably measured transversely to the direction of flow or in the circumferential direction) of 2 mm to 15 mm, preferably 7 mm to 12 mm. The term fenestration denotes so-called windows, open zones, or holes in the graft that, upon correct positioning of the stent graft in the affected area, are approximately congruent with a respective branching vessel in terms of position and diameter. The fenestrations are preferably configured to be oval or round, particularly preferably with a height-to-width ratio between 0.5 and 2.5, preferably between 0.8 and 2, particularly preferably between 1 and 1.35. Furthermore, scallops and/or fenestrations may be patient-specifically configured.

The graft may comprise one or more fenestrations and/or scallops, in particular in cases in which the area of the vessel wall alteration comprises a connection to a further vessel and/or the distance between the area of the vessel wall alteration and a connection to another vessel is less than 10 mm. The number of fenestrations may be between 0 and 10, preferably between 1 and 5. The fenestrations preferably have a diameter between 1 mm and 15 mm, particularly preferably between 3 mm and 12 mm or between 4 mm and 8 mm. The diameter of the one or more fenestrations is preferably at least 2 mm, at least 4 mm or at least 5 mm.

The stent structure is preferably provided on the graft such that the struts do not cross the fenestration or fenestrations and/or scallops and/or do not impair the blood flow through them.

According to the invention, relatively small fenestrations, for example, fenestrations having a diameter of, for example, 5 mm to 8 mm, may be provided between struts of the stent structure in the graft. In this respect, a pattern, in particular a regular pattern (for example, regular in the circumferential direction; e.g., a meander pattern having a specific amplitude and/or a specific interval) of the stent structure may be regular and/or unchanged in the area of the respective fenestration. For example, the amplitude and/or the interval of the pattern of the stent structure may remain unchanged in the area of the fenestration. Methods according to the invention may comprise a step of aligning the stent structure to be applied with the fenestration in the graft. In particular, this step of aligning may be a virtual alignment, preferably performed prior to the production of the stent structure, for example, in a CAD program (computer-aided design) and/or a CAM program (computer aided manufacturing).

As the case may be, fenestrations may be crossed by struts, for example, large fenestrations in the graft having a diameter of, for example, 8 mm to 15 mm. Preferably, however, the stent structure—in particular the strut pattern—may be adapted such that it is avoided or at least avoided to the greatest possible extent that a clearance opening of the fenestration is crossed and/or impaired. The stent structure and/or the struts of the stent structure may be guided around the fenestration, for example, in the case of a zigzag- or meander-shaped strut pattern, by changing (in particular increasing) the amplitude and/or the interval of the pattern in the area of the fenestration.

Alternatively or additionally, the arrangement of the struts may be configured such that edges of the fenestration are supported by struts. For example, the struts may pass around a respective fenestration at least partially (for example, over an angle of >90°, >180° or >270°) or completely in a circular and/or oval (for example, ellipsoid) manner.

Fenestrations and/or scallops may be provided, for example, by punching, perforating, cutting out, laser cutting, expanding and/or by means of, for example, flame shears. Preferably, however, the provided graft comprises one or more fenestrations and/or scallops that were already provided during its production (for example, by correspondingly weaving or knitting the graft). In this way, a subsequent local change in the material properties and/or a step of severing one or more of the threads forming the graft can be avoided. This is time-efficient since no reworking of the graft is required and no potential weak spots are generated in the graft. Therefore, the threads of the graft preferably are not severed in the area of the fenestrations and/or scallops and/or pass around these fenestrations and/or scallops.

The stent graft may optionally be branched at at least one end and/or at least one fenestration, wherein, e.g., a stent structure and/or a graft section protrudes into a branching blood vessel ("bifurcation" or "branch"). The branching section may be at least 0.5 cm, at least 1 cm or at least 3 cm long. This may help to ensure a stable position of a fenestration and/or to bridge, connect and/or seal the area between the graft and the branching vessel. Alternatively and/or additionally, the stent graft may also be in contact with at least one further stent structure and/or stent graft that is positioned or is being positioned in a further vessel that communicates with the affected vessel. In the case of such a modular structure, the contact may be achieved, for example, by partial overlapping.

The stent graft may be produced as a standardized or customized product. In particular in the case of fenestrations and/or bifurcations in and/or near the affected area, it may be advantageous to produce the stent graft for the affected vessel in a customized manner because the configuration and location of the bifurcation may vary considerably. Preferably, the stent graft is customized on the basis of image data of the affected vessel. In particular, the structure and/or the shape of the graft (for example, the location, shape and/or size of the one or more fenestrations) and/or the structure, shape and/or pattern of the stent structure (for example, the course of the struts and/or their cross-section) can be patient-specifically configured and/or produced on the basis of such image data.

Prior to the production of the graft and/or prior to the application of the stent structure onto the graft, information regarding the location of the affected area in the body, the dimension of the vascular segment to be supported or replaced as well as possible vascular branches located in or near the affected area may be obtained by medical imaging, in particular by means of a computed and magnetic resonance tomography, but optionally also by means of X-ray or ultrasonic devices, especially if they are suitable for recording a 3D image data set. As a basis for the production of a customized stent graft, the image data preferably have a slice thickness of at most 3 mm, preferably of at most 2 mm and particularly preferably of at most 1 mm. The data are preferably recorded transversely to the direction of flow at a distance of 0.05 mm to 10 mm, preferably at a distance of 0.5 mm to 3 mm. Two successive slices may have an overlap of at most 50%, preferably of at most 25%, wherein the distance between the slices is at most as large as the corresponding slice thickness. In order to ensure high-quality information regarding the exact configuration of the vessel wall, the images gathered and/or obtained are preferably postprocessed in a manner known to the person skilled in the art, for example, by means of multiplanar reconstruction, in order to provide a spatial resolution as high as possible in all spatial directions before they are used to produce a customized stent graft.

The gathered and/or provided image data may have been generated at one or more points in time and are used in a preferred method according to the invention to produce a computer-aided model of the graft, stent structure, and/or stent graft to configure a customized stent graft.

The computer-aided model(s), in particular a digital 3D model, may include the extent, 3D structure, and/or material properties of the stent graft, as well as information concerning the production, such as, for example, which materials are to be processed in which area of the stent graft and how. The model as a digital representation is preferably divided into cross-sectional slices by means of a computer system and/or CAD software, said cross-sectional slices being used to produce the vascular implant in a process of additive manufacturing. Preferably, the method for producing a stent graft according to the invention which has been customized on the basis of provided image data is fully automatable. The method according to the invention, in particular the direct application of the stent structure onto the graft, enables optimal customization and at the same time a considerably reduced production time.

In accordance with the method according to the invention, geometric data of the vessel may be used when defining the geometry of the graft (in particular, when generating the computer-aided model of the graft) and, in particular, may be fed into a computer-aided program. Alternatively or additionally, geometric data of the vessel and/or geometric data of the graft may be used when defining the geometry of the stent structure (in particular, when generating the computer-aided model of the stent structure) and, in particular, may be fed into a computer-aided program. The method may comprise, e.g., a step in which geometric data of the graft and geometric data of the stent structure (for example, the two computer-aided models) are combined in one program. This may, for example, allow the superimposition of the two computer-aided models, e.g., in a common computer-aided model and/or view.

Preferred embodiments of the invention are exemplarily described below with reference to the drawings. The drawings are merely schematic illustrations, which often do not show other (optional) structures in order to clarify certain aspects or which also take into account different optional aspects associated with each other in one illustration. In this context, the same reference signs indicate equivalent, similar, comparable or identical components in the represented embodiments.

The illustrated embodiments may be changed in many ways within the scope of protection of the claims. The disclosure of the Figures is not to limit the scope of protection of the invention. It should be noted that the features of the above mentioned embodiments may be combined in a single embodiment. Therefore, embodiments of the invention may comprise all or only some of the above-mentioned features, depending on their configuration.

Figure 1:
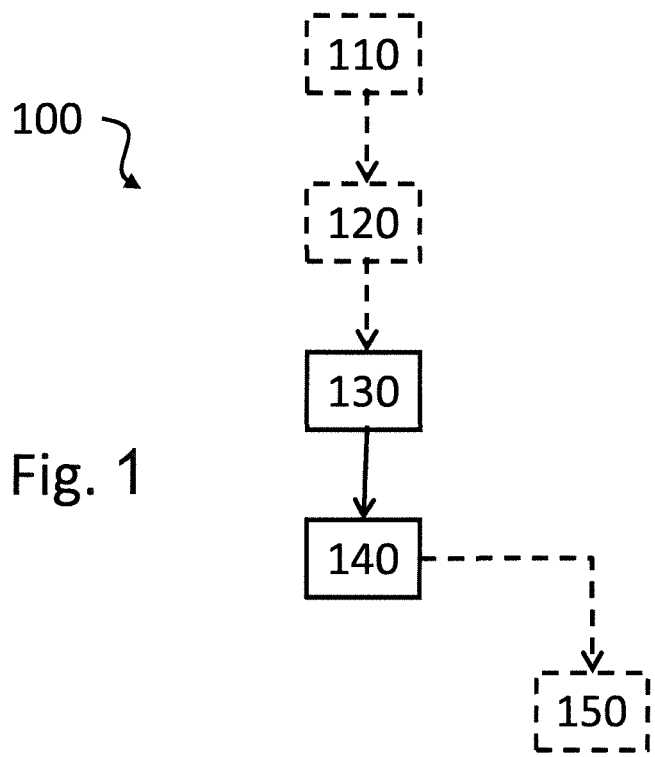
FIG. 1 shows a schematic flow chart of a method according to the invention.

FIG. 1 is a schematic flowchart illustrating the steps of a method 100 according to the invention for producing a stent graft 1 (see also FIG. 2), wherein dotted lines indicate optional steps. In a preferred embodiment of the method, preoperative medical image data of a vessel are first provided (step 110), which were gathered, for example, in the course of a computed and/or magnetic resonance tomography. The image data may be processed in a manner known to the person skilled in the art in order to obtain a 3-dimensional resolution as high as possible and may be used to generate a computer-aided model of the graft 10, the stent structure 20 and/or the stent graft 1 (step 120). The production of the stent graft 1 according to the invention, which is preferably customized, is accomplished by providing (step 130) a preferably polymer-based graft 10 onto which a stent structure 20 comprising a plurality of struts made of a preferably polymer-based material is applied (step 140). This is preferably done by means of fused deposition modeling as an additive manufacturing process. The stent graft 1 according to the invention may be optionally inverted (step 150) after the stent structure has been applied in step 140, for example, in order to arrange the stent structure 20 within the graft 10.

Figure 2:
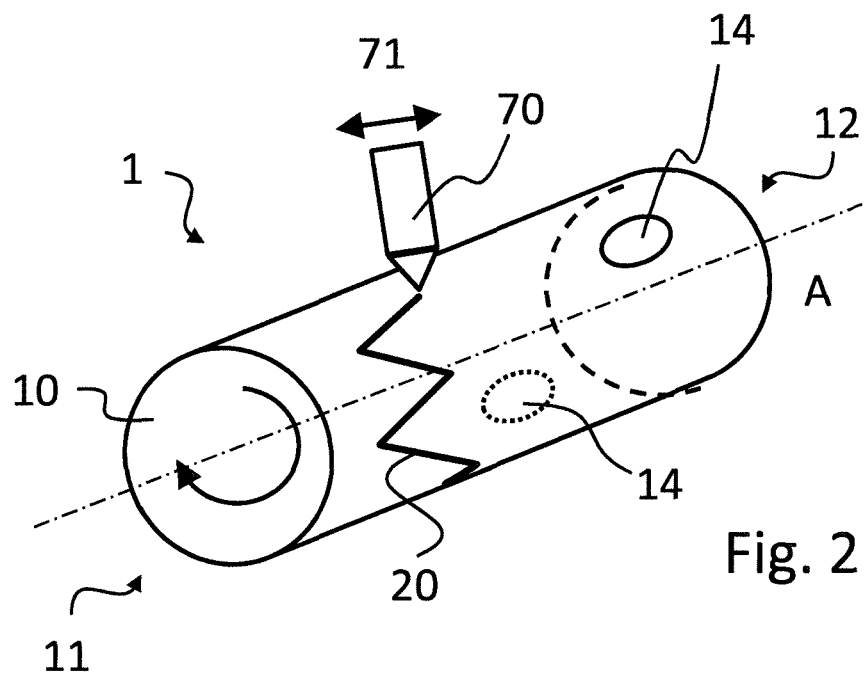
FIG. 2 shows a schematic illustration of the application of the stent structure onto a graft according to the invention.

FIG. 2 is a perspective view schematically illustrating a production of the preferably tubular and/or tube-shaped, in particular hollow-cylindrical stent graft 1, which preferably extends from a first open end 11 to an opposite, second open end 12. The graft 10 preferably being textile-based or consisting of textile may be slid onto and/or rest on a holder (not shown). The holder may be rotatably mounted, for example such that the graft 10 may be rotated around its longitudinal axis A. The geometry of the holder may be selected according to the geometry of the graft 10, in particular, the outer diameter of a cylindrical holder may be selected according to the vessel diameter to be treated.

The tubular graft 10 exemplarily shown in this Figure comprises two fenestrations 14, which are shown here in the area of the second end 12. However, these fenestrations may also be provided at other locations of the graft along the longitudinal axis A (e.g., in the middle). Additionally and/or alternatively, the graft 10 could also comprise at least one scallop, further fenestrations and/or branches, so-called branch stents ("branches"), along the longitudinal axis A. In addition and/or alternatively, the graft 10 may also comprise further openings at the ends 11, 12 or it could be bifurcated ("bifurcation", not shown) at one of these ends 11, 12.

The stent structure 20 is preferably applied directly onto the graft 10 in that polymer-based or polymeric material provided therefor is heated in a heatable nozzle head 70 and one or more liquefied filaments are applied 140 onto the graft 10 in one or more layers. This may be done, for example, in an automated method according to a computer-aided model of the stent graft 1 generated in step 120, while the nozzle head 70 moves essentially along the longitudinal direction of the graft 10 (see arrow 71) and the holder rotates as needed. Alternatively, the holder may also be moved essentially in the longitudinal direction or the holder and the nozzle head 70. The thus formed plurality of interconnected struts of the stent structure 20 may optionally be arranged as rings, zigzag, helix, spirals, meshes and/or other geometry, wherein, for example, individual segments of the stent structure may be directly or indirectly connected to each other via connectors.

Figure 3A:
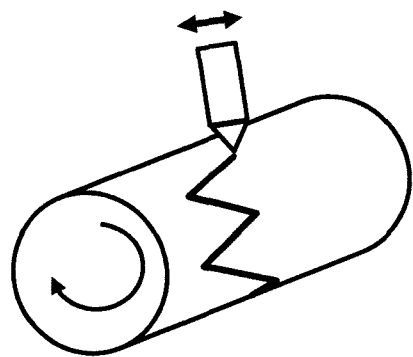
FIG. 3 shows a schematic illustration of the stent graft according to the invention in a compressed and an expanded state.
Figure 3B:
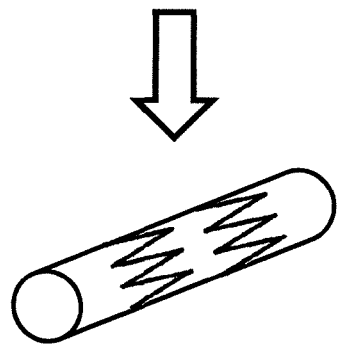
Figure 3C:
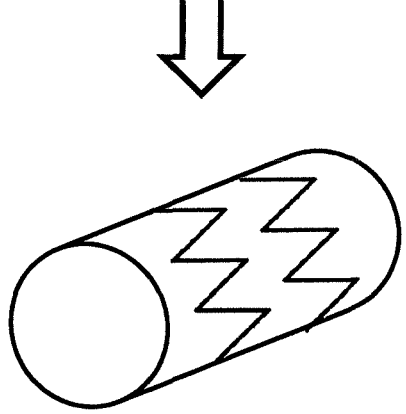

The stent graft 10 may be inserted into a vessel in a known manner. FIG. 3 shows a schematic overview of various states that the stent graft may at least exhibit, with the change in state being preferably reversible and rapid due to the material and/or material combination of the stent structure. During its production, the stent graft may initially exhibit a first state (FIG. 3A). For example, the stent graft may be produced in an expanded state. After its production, but at the latest before its insertion into the affected vessel, preferably endovascular and/or minimally invasive, the stent graft exhibits a compressed, crimped state (FIG. 3B). For this purpose, depending on the stent geometry, for example, the opening angle between two struts connected at a junction and/or intersection point may be reduced. After the stent graft has been positioned in the affected portion of the vessel, it is transformed into an expanded state, in which it has a larger diameter than in the at least one crimped state (FIG. 3C), wherein the expanded state may optionally correspond to the first state. This change in state may be caused by the application of a mechanical force or in a predefined way by the change of an external factor if a respective smart polymer was used to form the stent structure (e.g., by returning to an expanded shape when the temperature is increased). In this case, the expanded state is preferably achieved by reaching the body temperature and thus a temperature of 37° C.

In the expanded state, the stent structure preferentially exhibits a radial stiffness that is sufficient to bridge or replace the affected portion of the vessel. The graft is preferably configured as a self-sealing system that is initially permeable to liquid and, upon implantation of the stent graft, seals itself within a short time by coagulation of components contained in the liquid transported in the vessel and/or their deposition in and/or on the graft.

As far as the above description uses the expression "essentially" or corresponding terms, embodiments in which the respective feature is fully or completely present are also comprised. The words "plurality" or "several" are to be understood in the sense of "at least two", i.e., two or more. If specific values are indicated, these values preferably also comprise minor deviations from these values, such as, for example, deviations of +/−10% or +/−5% of the respective value. Individual aspects of the invention may constitute independent inventions and may also be claimed as such.

The invention claimed is:

1. A method for producing a stent graft, which comprises the following steps:
   providing a graft made of a first polymer-based material; and
   then applying a stent structure comprising a plurality of struts made of a second polymer-based material onto the graft by means of an additive method;
   wherein the graft and the applied stent structure are configured such that the stent graft is arrangeable in at least one compressed state and in at least one expanded state, wherein the stent graft has a smaller cross-section in the at least one compressed state than in the at least one expanded state.

2. The method according to claim 1, wherein the graft is tubular and/or tube-shaped.

3. The method according to claim 1, wherein the produced stent graft is configured such that the graft is arranged within the stent structure.

4. The method according to claim 1, wherein the graft is textile and/or textile-based.

5. The method according to claim 4, wherein the graft is a weave and/or knitwear.

6. The method according to claim 1, wherein the graft is produced by means of a jacquard technique.

7. The method according to claim 1, wherein the stent structure comprises a shape memory polymer.

8. The method according to claim 1, wherein the provided graft comprises fenestrations.

9. The method according to claim 8, wherein the fenestrations have a diameter between 3 mm and 12 mm.

10. The method according to claim 1, wherein the provided graft comprises a plurality of pores formed by a textile structure of the graft and having a diameter of 1 to 1,000 µm.

11. The method according to claim 10, wherein individual pores have an opening area of 1 to 1,000,000 µm$^2$.

12. The method according to claim 1, wherein the struts, in a cross-section perpendicular to the direction in which the respective strut extends, have a height of at least 10 µm in the radial direction of the stent graft and/or a width perpendicular to the height of at least 10 µm in the cross-section.

13. The method according to claim 1, wherein the struts, in a cross-section perpendicular to the direction in which the respective strut extends, in the radial direction of the stent graft, are made from a plurality of layers, and/or wherein the struts, in a cross-section perpendicular to the direction in which the respective strut extends, perpendicular to the radial direction of the stent graft, comprise a plurality of layers.

14. The method according to any claim 1, which further comprises the steps of:
   obtaining preoperative medical image data of a vessel; and
   generating a computer-aided model of the graft the stent structure and/or the stent graft by means of the image data.

15. The method according to claim 1, wherein the stent structure is applied onto the graft by using a rotatable holder by means of which the graft can be held and rotated.

16. The method according to claim 1, wherein the struts configure a compressible helical, zigzag or mesh structure and/or meander-shaped rings.

17. The method according to claim 1, wherein the graft comprises one or more scallops.

18. The method according to claim 1, wherein the graft has a material layer thickness of 0.01 mm to 2 mm after its production.

19. The method according to claim 1, wherein the provided graft is configured to be permeable to liquid and wherein the graft forms a self-sealing system.

20. The method according to claim 1, wherein the provided graft is impermeable to liquid.

21. The method according to claim 20, wherein the provided graft is impermeable to liquid by means of a coating, wherein the method comprises a step of coating the graft before the application of a stent structure onto the graft.

22. The method according to claim 20, wherein the provided graft is impermeable to liquid by means of a coating, wherein, after the application of a stent structure onto the graft, the method comprises a step of coating the produced stent graft.

23. The method according to claim 1, wherein the stent graft comprises at least one stent structure that is arranged on the graft at least partially inside and outside, and/or wherein the stent graft comprises at least one stent structure that is arranged on an inner side of the graft and at least one stent structure that is arranged on an outer side of the graft.

24. The method according to claim 1, wherein the stent graft is metal-free.

25. A stent graft, produced according to the method of claim 1.

26. The stent graft of claim 25, wherein the stent structure surrounds the graft.

27. The method according to claim 1, wherein the additive method is fused deposition modeling.

28. The method according to claim 1, wherein the stent structure is applied directly onto the graft by means of the additive method.

29. The method according to claim 1, wherein the stent structure is attached to the graft when applying said stent structured onto the graft by means of said additive method.

* * * * *